(12) United States Patent
Nonboe et al.

(10) Patent No.: US 10,251,731 B2
(45) Date of Patent: Apr. 9, 2019

(54) METHOD FOR DIGITAL DESIGNING A DENTAL RESTORATION

(71) Applicant: 3SHAPE A/S, Copenhagen K (DK)

(72) Inventors: Sven Nonboe, Hillerød (DK); Rune Fisker, Virum (DK)

(73) Assignee: 3SHAPE A/S, Copenhagen K (DK)

( * ) Notice: Subject to any disclaimer, the term of this patent is extended or adjusted under 35 U.S.C. 154(b) by 0 days.

(21) Appl. No.: 15/455,735

(22) Filed: Mar. 10, 2017

(65) Prior Publication Data

US 2017/0258561 A1    Sep. 14, 2017

(30) Foreign Application Priority Data

Mar. 10, 2016   (DK) ................................ 2016 70139

(51) Int. Cl.
| | |
|---|---|
| *A61C 5/77* | (2017.01) |
| *A61C 9/00* | (2006.01) |
| *A61C 11/00* | (2006.01) |
| *A61C 13/00* | (2006.01) |
| *A61C 19/05* | (2006.01) |
| *G06F 17/50* | (2006.01) |

(52) U.S. Cl.
CPC ............ *A61C 13/0004* (2013.01); *A61C 5/77* (2017.02); *A61C 9/0046* (2013.01); *A61C 11/00* (2013.01); *A61C 19/05* (2013.01); *G06F 17/50* (2013.01)

(58) Field of Classification Search
None
See application file for complete search history.

(56) References Cited

U.S. PATENT DOCUMENTS

| | | | | |
|---|---|---|---|---|
| 2009/0068617 | A1* | 3/2009 | Lauren | A61C 13/0004 433/213 |
| 2013/0066598 | A1* | 3/2013 | Fisker | A61C 11/00 703/1 |
| 2015/0111177 | A1* | 4/2015 | Fisker | A61C 13/01 433/196 |
| 2016/0157967 | A1* | 6/2016 | Kim | A61C 1/084 433/201.1 |

FOREIGN PATENT DOCUMENTS

| | | |
|---|---|---|
| EP | 1 661 529 A2 | 5/2006 |
| EP | 2 468 212 A2 | 6/2012 |
| EP | 2 974 690 A1 | 1/2016 |
| WO | WO 2005/055861 A2 | 6/2005 |

* cited by examiner

*Primary Examiner* — Whitney Moore
(74) *Attorney, Agent, or Firm* — Buchanan Ingersoll & Rooney P.C.

(57) ABSTRACT

Disclosed is a method for digitally designing a dental restoration, wherein a 3D representation of at least a part of the upper or lower jaw is obtained. The 3D representation represents at least a target site for placing the final restoration and at least one antagonist tooth opposing the target site. Furthermore a digital anatomy design of the restoration is provided. The digital anatomy is based at least on a dynamic occlusion and a relative offset of the planned restoration position. Accordingly, a restoration may be designed that does not interrupt the natural occlusion.

3 Claims, 4 Drawing Sheets

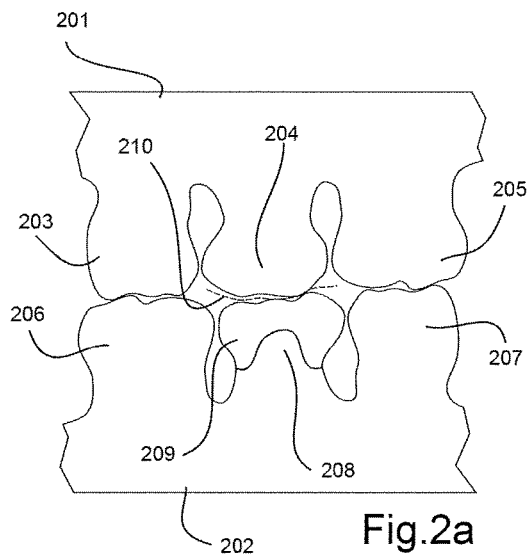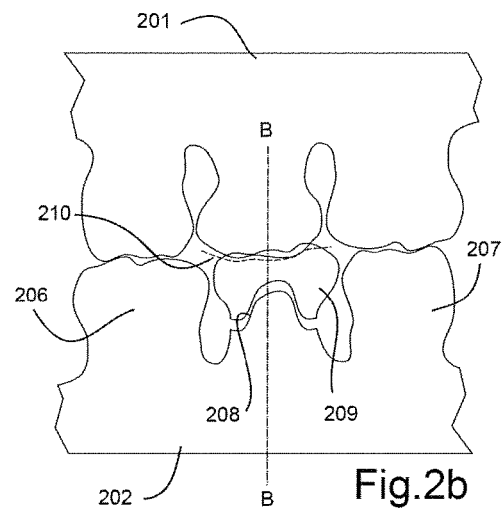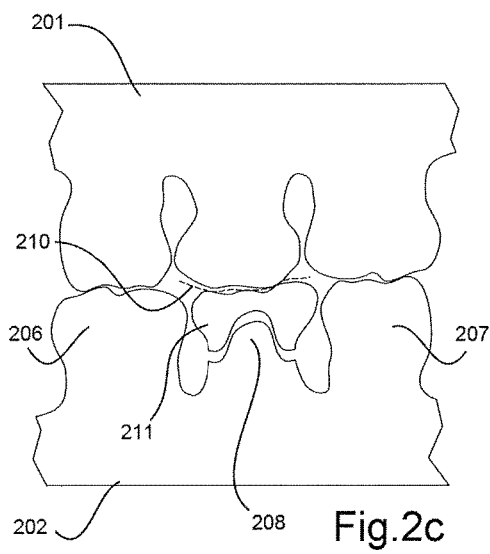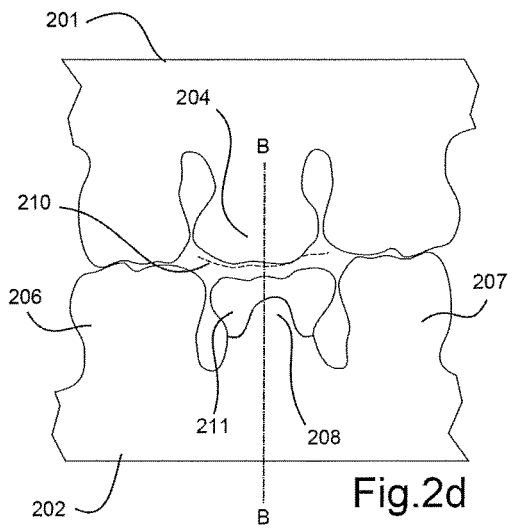

METHOD FOR DIGITAL DESIGNING A DENTAL RESTORATION

FIELD OF THE INVENTION

This invention generally relates to digitally designing a dental restoration. In particular it relates to a method for digitally designing a dental restoration where the risk that the dental restoration interferes with the current occlusion/bite of the patient is reduced.

BACKGROUND OF THE INVENTION

When doing restorative work on a patient the dentist always has to be careful not to alter the occlusion of the patient. A changed occlusion may result in a change in chewing motion and bite and may cause discomfort or even pain.

Accordingly, it is a desire to prevent, or at least reduce the risk, that the occlusion is altered during restorative work.

SUMMARY

Disclosed is a method for digitally designing a dental restoration, comprising:
  obtaining a 3D representation of at least a part of an upper or lower jaw of a patient, representing at least a target site for placing the restoration and at least one antagonist tooth opposing the target site,
  providing a digital anatomy design of the restoration based at least on a dynamic occlusion and a relative offset of the planned restoration position.

This has the effect that the anatomy design of the dental restoration can be designed slightly lower than the surrounding teeth and thus the occlusion of the patient is maintained.

It has even been shown that in many cases the restoration, if it is based on a natural tooth, will naturally move towards the antagonist until in contact during occlusion.

Accordingly, a restoration may be designed that does not interrupt the natural occlusion and in many cases will in time place itself in a natural position.

Unless specifically stated herein any reference to occlusion should be understood as dynamic occlusion, i.e. the contact between teeth during movement of a jaws when closed. For example, occlusion does not refer to static occlusion.

In one embodiment the step of providing the digital anatomy design comprises,
  determining an occlusion boundary defined by the at least one antagonist tooth during the dynamic occlusion,
  providing the relative offset by offsetting the occlusion boundary relative to the target site,
  generating the digital anatomy design within the occlusion boundary and the neighboring teeth.

This advantageously allows the design of the digital anatomy design in one step, basically automating the anatomy design step.

In other situations, it may be desirable to modify an existing design.

Accordingly, in another embodiment the method comprises the steps of,
  designing at least an intermediate anatomy of the restoration, and
  wherein the step of providing a digital anatomy design further comprises the steps of,
    determining contact areas between the at least one antagonist tooth and the intermediate anatomy of the restoration based on the dynamic occlusion and the relative offset,
    generating the anatomy design of the restoration by modifying the shape of the intermediate anatomy of the restoration at least in the contact areas.

In one embodiment the relative offset is provided by arranging the intermediate anatomy with a predetermined offset distance away from the target site.

This is particularly advantageous as it allows the contact areas to be determined by performing the dynamic occlusion while the intermediate anatomy is arranged in a relative offset away from the target site.

In yet another embodiment the relative offset is represented as a threshold distance applied for determining the contact areas during dynamic occlusion.

In one embodiment, the method further comprises that
  the contact areas are determined by establishing an occlusion surface by tracing the relative teeth movement opposite the target site during dynamic occlusion, and providing the relative offset by offsetting the occlusion surface towards the target site, and
  that the anatomy design is generated by using the offset occlusion surface as a cutting surface on the intermediate anatomy.

In addition, when providing an occlusion surface it is not necessary to rerun the dynamic occlusion every time changes are done to the anatomy design, since the occlusion surface shows if there are any areas that need to be modified or reshaped/remodeled.

In general the relative offset can be provided in many different ways, for example the relative offset is provided by offsetting the target site relative to the jaw, or by offsetting the intermediate anatomy relative to the antagonist, or by offsetting the intermediate anatomy relative to the target site.

Disclosed is also a nontransitory computer readable medium storing thereon a computer program, where said computer program is configured for executing the steps of the method disclosed herein.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIG. 2a-2d shows the design steps of a method according to another embodiment of the invention.

DETAILED DESCRIPTION

Figure 1A:
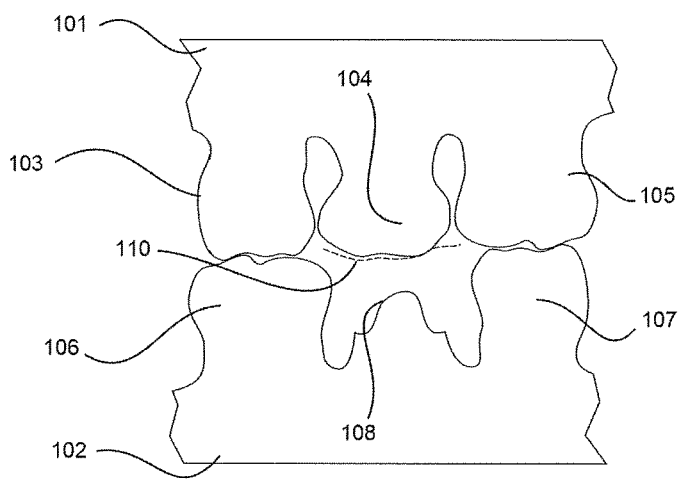
FIG. 1a-1c shows the design steps of a method according to one embodiment of the invention.

FIG. 1a shows an upper digital dental model (upper model) 101 and lower digital dental model (lower model) 102. The digital dental models represents a section of a patients jaw and have been acquired by scanning the respective section of the jaw with an intra oral scanner, for example the TRIOS manufactured by 3Shape TRIOS. The digital dental models could also be obtained from scanning a physical impression or a gypsum model, which both are method known in the art for obtaining digital dental models.

The upper model 101 has digital representations of three molar teeth 103, 104, 105 and the lower model 102 has digital representations of two molar teeth 106, 107 separated by a target site 108 which in this case is a prepared tooth.

The dynamic occlusion of the jaw is found by placing the dental models in a virtual/digital articulator. Such virtual articulators are well known and are computer driven simulations and representations of physical articulators, which are used to estimate the jaw movement and occlusion of a patient. By using the representations of the existing teeth 103, 104, 105, 106 and 107 as limitation during dynamic occlusion a very close estimation of the natural dynamic occlusion can be found. In addition, an occlusion surface 110 is found by tracing the surface of the middle molar 104 opposing the preparation during dynamic occlusion.

Figure 1B:
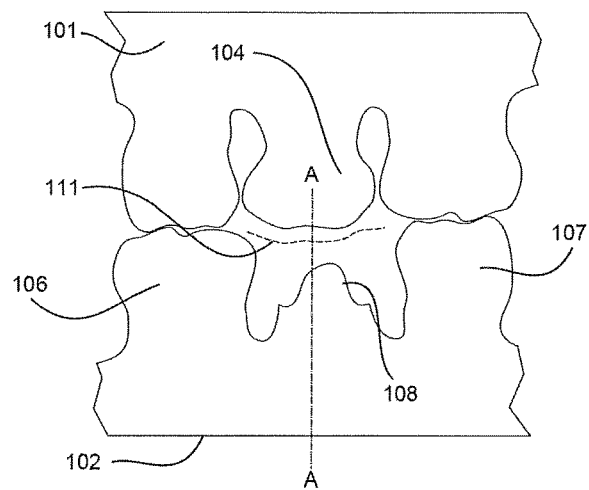

The occlusion surface is subsequently offset 111 a desired distance towards the target site along axis A-A as shown in FIG. 1b.

Figure 1C:
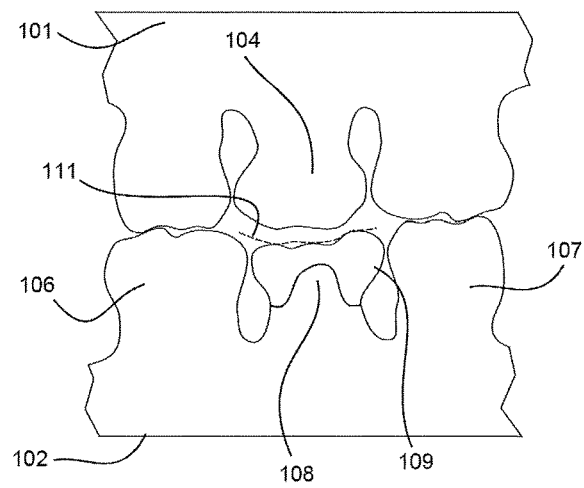

A restoration, such as a crown 109 as shown in FIG. 1c with a digital anatomy design is now modeled on the prepared tooth 108 using the offset occlusion surface 111 and the neighboring teeth 106, 107 as design boundaries.

As can be understood, the digital anatomy design is thus retracted and therefore does not interfere with the occlusion of the existing teeth represented by teeth models 102, 103, 104, 105, 106 and 107.

In another embodiment an upper digital dental model (upper model) 201 and lower digital dental model (lower model) 202 is obtained, for example by means as previously described above.

The upper model 201 has digital representations of three molar teeth 203, 204, 205 and the lower model 202 has digital representations of two molar teeth 206, 207 separated by a target site 208 which in this case is a prepared tooth as shown in FIG. 2a.

An occlusion surface 210 is provided by virtual articulation as discussed previously, e.g. in connection with FIGS. 1a-1c above.

An intermediate anatomy design 209 of the restoration is provided on the target site.

A relative offset of the intermediate anatomy design 209 is provided as shown in FIG. 2b by offsetting the intermediate anatomy design 209 along axis B-B away from the target site 208.

Based on the occlusion surface 210 the intermediate anatomy design 209 is modified as shown in FIG. 2c. This results in a modified anatomy design 211, which follows the constraints applied by the software as a result of the occlusion surface 210.

Subsequently, as shown in FIG. 2d, the modified anatomy design 211 is placed on the target site 208 and the dental technician can verify the fit e.g. against the neighboring teeth 206 and 207 and provide further modifications if necessary.

As previously discussed the disclosed method provides a retracted digital anatomy design that does not interfere with the occlusion of the existing teeth represented by teeth models 202, 203, 204, 205, 206 and 207.

Figure 3A:
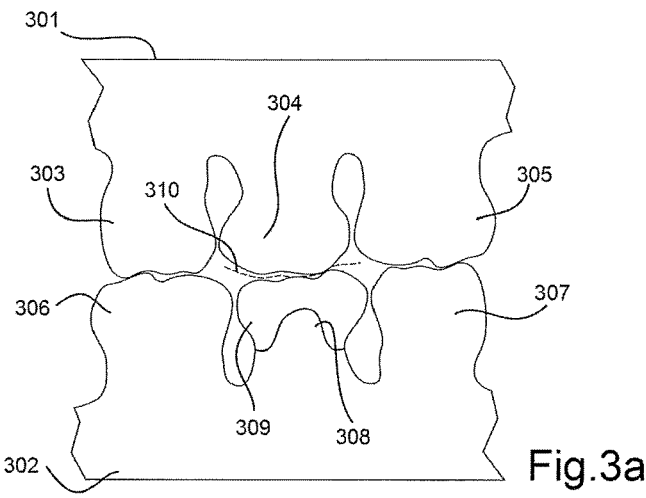
FIG. 3a-3c shows the design steps of a method according to yet another embodiment of the invention.
Figure 3B:
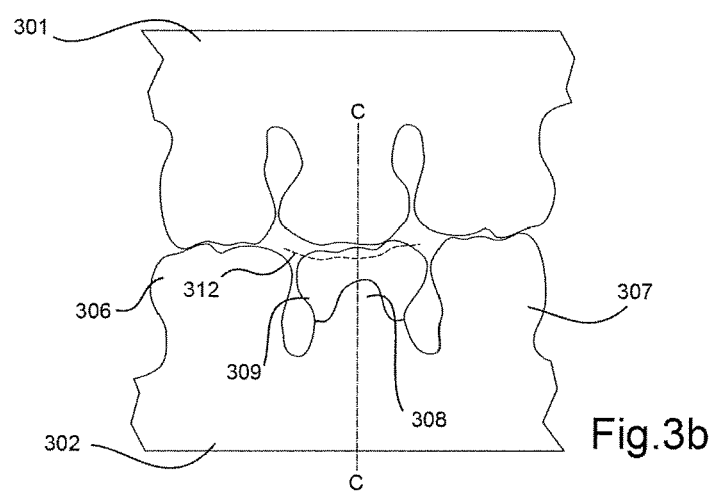
Figure 3C:
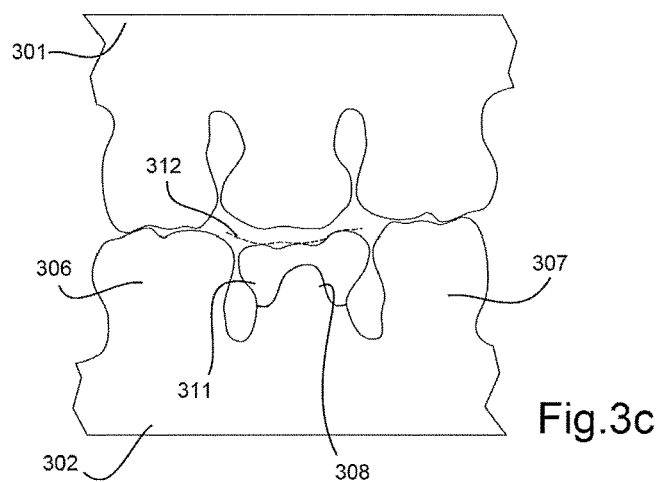

In a third embodiment as shown in FIGS. 3a-3c the digital steps for designing a restoration are shown.

A 3D representation of an upper model of the jaw 301 and the lower model of the jaw 302 is obtained. E.g. as disclosed previously in connection with other embodiments or as known in the art. An upper model 301 is provided and has digital representations of three molar teeth 303, 304, 305 and the lower model 302 has digital representations of two molar teeth 306, 307 separates by a target site 308 which in this case is a prepared tooth.

An occlusion surface 310 is provided by virtually articulating the jaws and tracing the surface of the molar tooth representation 304 during dynamic occlusion, for example as previously described.

An intermediate anatomy design 309 of a dental restoration is designed using the antagonist tooth 304, the occlusion surface 310 and the neighboring teeth 306 and 307 as design boundaries.

The occlusion surface 310 is offset 312 by shifting it towards the target site 308 along line C-C as shown in FIG. 3b.

A modified anatomy design 311 is subsequently provided by using the offset occlusion surface 312 as a design boundary.

Again, the digital anatomy design is thus retracted and therefore does not interfere with the occlusion of the existing teeth represented by teeth models 302, 303, 304, 305, 306 and 307.

Other embodiments of digital design methods for providing a digital anatomy design as disclosed herein may be provided within the scope of the claimed invention.

The method for digitally designing a restoration is provided on computation means for executing the method before a user, such as a dental technician.

Figure 4:
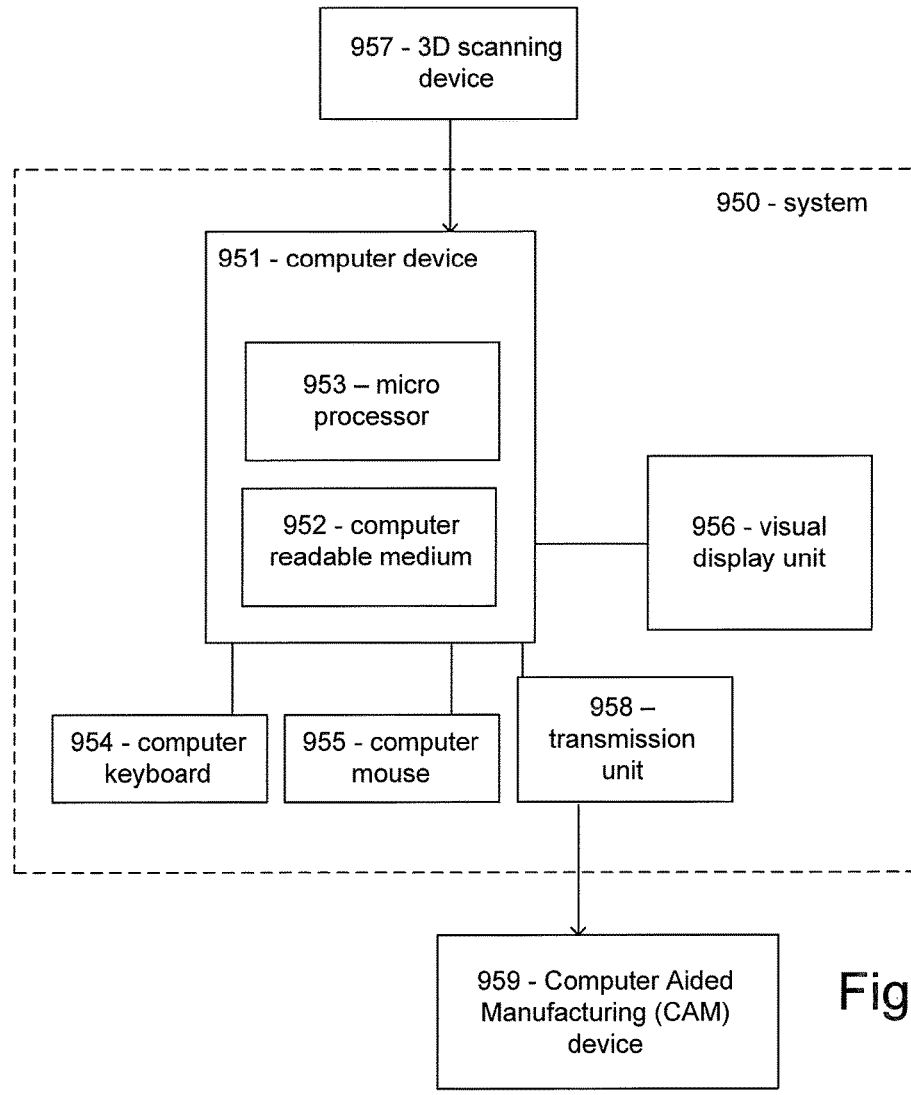
FIG. 4 shows an embodiment of computer system suitable for working the method disclosed herein.

For example, the method is provided in a computer system as shown in FIG. 4. The computer system 950 comprises a computer device 951 comprising a computer readable medium 952 and a processor 953. The system further comprises a visual display unit 956, a computer keyboard 954 and a computer mouse 955 for entering data and activating virtual buttons visualized on the visual display unit 956. The visual display unit 956 can be a computer screen/monitor. The computer device 951 is capable of receiving a digital 3D representation of the patient's set of teeth from a scanning device 957, such as the TRIOS intra-oral scanner manufactured by 3shape A/S, or capable of receiving scan data from such a scanning device and forming a digital 3D representation of the patient's set of teeth based on such scan data. The received or formed digital 3D representation can be stored in the computer readable medium 952 and provided to the processor 953. The processor 953 is configured for executing computer code that allows for the steps of the method for digitally designing a restoration as disclosed herein. The user is guided through the method steps via a user interface visualized on the visual display unit 956.

The computer system comprises a unit 958 for transmitting the virtual 3D model to e.g. a computer aided manufacturing (CAM) device 959 for manufacturing the dental restoration or to another computer system e.g. located at a milling center where the dental restoration is manufactured. The unit for transmitting the virtual 3D model can be a wired or a wireless connection.

Alternatively, or in combination with the computer system as disclosed a cloud based system can be implemented. For example data used for the design steps can be stored remotely on external servers. Such servers could be placed abroad and accessed via the Internet. Even further, the process, or parts thereof, could also be executed on the external servers, such that the user is simply presented with the result of such processes on a visual display unit while the processing occurs remotely.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

The invention claimed is:

1. A method for digitally designing a dental restoration using a computer having a non-transitory medium having instructions which cause the computer to digitally design the dental restoration, the method comprising:

obtaining a 3D representation of at least a part of an upper or lower jaw of a patient, representing at least a target site for placing the restoration and at least one antagonist tooth opposing the target site, providing a digital anatomy design of the restoration based at least on a dynamic occlusion and a relative offset of the planned restoration position by establishing an occlusion surface and providing the relative offset by offsetting the occlusion surface towards the target site, wherein the method further comprises the steps of, designing at least an intermediate anatomy of the restoration, and wherein the step of providing a digital anatomy design further comprises the steps of, determining contact areas between the at least one antagonist tooth and the intermediate anatomy of the restoration based on the dynamic occlusion and the relative offset, generating the anatomy design of the restoration by modifying the shape of the intermediate anatomy of the restoration at least in the contact areas, further comprising that the contact areas are determined by establishing the occlusion surface by tracing the relative teeth movement opposite the target site during dynamic occlusion, and that the anatomy design is generated by using the offset occlusion surface as a design boundary on the intermediate anatomy.

2. A method according to claim 1, wherein the relative offset is represented as a threshold distance applied for determining the contact areas during dynamic occlusion.

3. A method according to claim 1, wherein determining contact areas between the at least one antagonist tooth and the intermediate anatomy of the restoration based on the dynamic occlusion and the relative offset comprises determining all contact areas between the at least one antagonist tooth and the intermediate anatomy of the restoration.

* * * * *